US006430434B1

(12) United States Patent
Mittelstadt

(10) Patent No.: US 6,430,434 B1
(45) Date of Patent: Aug. 6, 2002

(54) METHOD FOR DETERMINING THE LOCATION AND ORIENTATION OF A BONE FOR COMPUTER-ASSISTED ORTHOPEDIC PROCEDURES USING INTRAOPERATIVELY ATTACHED MARKERS

(75) Inventor: Brent D. Mittelstadt, Placerville, CA (US)

(73) Assignee: Integrated Surgical Systems, Inc., Davis, CA (US)

( * ) Notice: Subject to any disclaimer, the term of this patent is extended or adjusted under 35 U.S.C. 154(b) by 0 days.

(21) Appl. No.: 09/458,358

(22) Filed: Dec. 9, 1999

Related U.S. Application Data
(60) Provisional application No. 60/112,321, filed on Dec. 14, 1998.

(51) Int. Cl.[7] ............................................... A61B 5/103
(52) U.S. Cl. .................... 600/426; 600/429; 606/130
(58) Field of Search .................... 600/411, 414, 600/417, 426, 427, 429; 606/130; 128/922, 920

(56) References Cited

U.S. PATENT DOCUMENTS

| | | |
|---|---|---|
| 4,146,924 A | 3/1979 | Birk et al. |
| 4,373,532 A | 2/1983 | Hill et al. |
| 4,841,975 A | 6/1989 | Woolson |
| 4,932,414 A | 6/1990 | Coleman et al. |
| 4,945,914 A | 8/1990 | Allen |
| 4,991,579 A | 2/1991 | Allen |
| 5,016,639 A | 5/1991 | Allen |
| 5,086,401 A | 2/1992 | Glassman et al. |
| 5,094,241 A | 3/1992 | Allen |
| 5,097,839 A | 3/1992 | Allen |
| 5,119,817 A | 6/1992 | Allen |
| 5,142,930 A | 9/1992 | Allen et al. |
| 5,161,536 A | 11/1992 | Vilkomerson et al. |
| 5,167,165 A | 12/1992 | Brucher et al. |
| 5,178,164 A | 1/1993 | Allen |
| 5,180,382 A | 1/1993 | Frigg et al. |

(List continued on next page.)

FOREIGN PATENT DOCUMENTS

| | | | | |
|---|---|---|---|---|
| EP | 647428 | 12/1995 | | |
| WO | WO 91/07726 | 5/1991 | | |
| WO | WO 94/17733 | 8/1994 | | |
| WO | WO 96 11624 | * | 4/1996 | ................. 600/426 |
| WO | WO 97/09929 | 3/1997 | | |

OTHER PUBLICATIONS

Cain, et al., "Safety considerations in a surgical robot", Integrated Surgical Systems, Inc., Sacramento, California, Paper #93–035, pp. 291–294, (1993).

Kazanzides, et al., "Surgical and industrial robots: Comparison and case study", Integrated Surgical Systems, Inc., Sacramento, California, vol. 10, pp. 10–19 to 10–26 (circa 1994).

Kazanzides, et al., "Architecture of a surgical robot", IEEE Conference on Systems, Man, and Cybernetics, pp. 1624–1629, (1992).

(List continued on next page.)

*Primary Examiner*—Ruth S. Smith
(74) *Attorney, Agent, or Firm*—Townsend and Townsend and Crew LLP

(57) ABSTRACT

A method for re-registration between a robotic coordinate system and an image data set, said method comprising: providing an image data set that has been registered within a robotic coordinate system based upon an initial bone position within the robotic coordinate system; locating at least three conserved points fixed relative to the initial bone position prior to any detectable change in bone position from the initial bone position; relocating the same three conserved point after bone motion may have occurred to determine the locational change in the three conserved points; and re-register the image data set within the robotic coordinate system based on the locational changes.

5 Claims, 5 Drawing Sheets

U.S. PATENT DOCUMENTS

| | | |
|---|---|---|
| 5,198,877 A | 3/1993 | Schulz |
| 5,211,164 A | 5/1993 | Allen |
| 5,222,499 A | 6/1993 | Allen et al. |
| 5,230,338 A | 7/1993 | Allen et al. |
| 5,236,432 A | 8/1993 | Matsen, II et al. |
| 5,249,581 A | 10/1993 | Horbal et al. |
| 5,299,288 A | 3/1994 | Glassman et al. |
| 5,306,306 A | 4/1994 | Bisek et al. |
| 5,320,115 A | 6/1994 | Kenna |
| 5,343,877 A | 9/1994 | Park |
| 5,383,454 A | 1/1995 | Bucholz |
| 5,394,457 A | 2/1995 | Leibinger et al. |
| 5,394,875 A | 3/1995 | Lewis et al. |
| 5,397,329 A | 3/1995 | Allen |
| 5,408,409 A | 4/1995 | Glassman et al. |
| 5,411,503 A | 5/1995 | Hollstien et al. |
| 5,480,400 A | 1/1996 | Berger |
| 5,524,180 A | 6/1996 | Wang et al. |
| 5,546,942 A | 8/1996 | Zhang |
| 5,551,429 A * | 9/1996 | Fitzpatrick et al. ......... 600/426 |
| 5,564,437 A | 10/1996 | Bainville et al. |
| 5,590,215 A | 12/1996 | Allen |
| 5,622,170 A * | 4/1997 | Schulz ...................... 600/427 |
| 5,649,021 A | 7/1997 | Matey et al. |
| 5,674,221 A | 10/1997 | Hein et al. |
| 5,682,886 A | 11/1997 | Delp et al. |
| 5,696,837 A | 12/1997 | Green |
| 5,769,078 A | 6/1998 | Kliegis |
| 5,772,594 A | 6/1998 | Barrick |
| 5,799,055 A | 8/1998 | Peshkin et al. |
| 5,806,518 A | 9/1998 | Mittelstadt |
| 5,807,252 A * | 9/1998 | Hassfeld et al. ............ 606/130 |
| 5,824,085 A | 10/1998 | Sahay et al. |
| 5,868,675 A | 2/1999 | Henrion et al. |
| 5,971,997 A | 10/1999 | Guthrie et al. |
| 6,011,987 A | 1/2000 | Branett |

OTHER PUBLICATIONS

Kazanzides, et al., "Force sensing and control for surgical robot", IEEE Intl. Conference on Robotics and Automation, pp. 612–617, (May 1992).

Lavallee, et al., "Computer assisted spine surgery: A technique for accurate transpedicular screw fixation using CT data and a 3–D optical localizer", TIMC, Faculte de Medecine de Grenoble, La Tronche, France, pp. 315–322 (1995).

Lombardi, Adolph V., "Cement removal in revision total hip arthroplasty", Seminars in Arthroplasty, 3(4):264–272, (Oct. 1992).

Mittelstadt et al., "Robotic surgery: Achieving predictable results in an unpredictable environment", Integrated Surgical Systems, Inc., Sacramento, California, pp. 367–372, (1993).

Mittelstadt et al., "The evolution of a surgical robot from prototype to human clinical use", Integrated Surgical Systems, Inc., Sacramento California, pp. 36–41, (1994).

Mittelstadt et al., "Development of a surgical robot for cementless total hip replacement", Robotics, 11:553–560, (1993).

Nolte, et al., "A novel approach to computer assisted spine surgery", M.E. Muller Institute for Biomechanics, University of Bern, Bern, Switzerland a pp. 323–328 (1995).

Paul et al., "Development of a surgical robot for cementless total hip arthroplasty", Clinical Orthopaedics, 285:57–66, (1992).

* cited by examiner

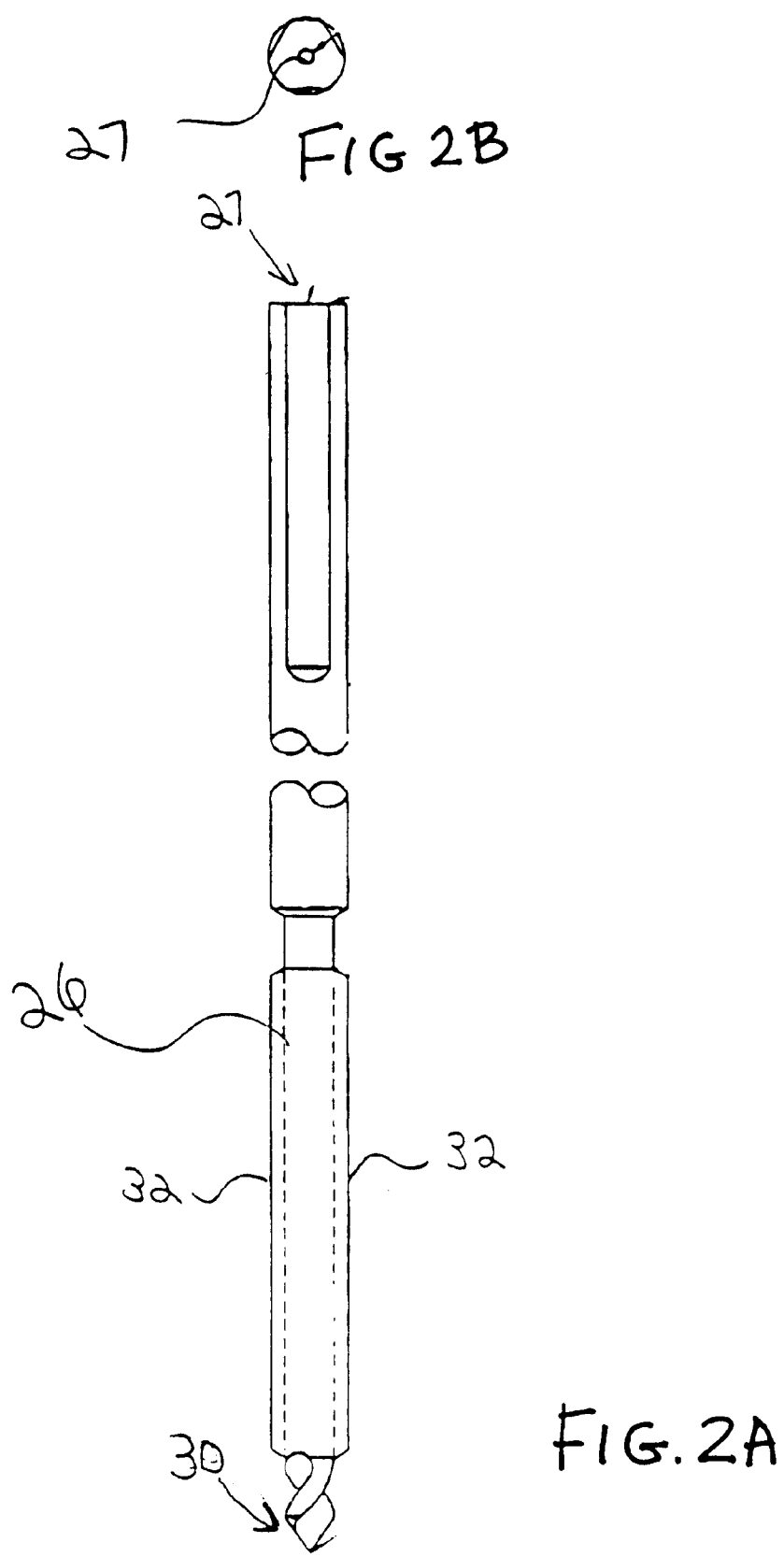

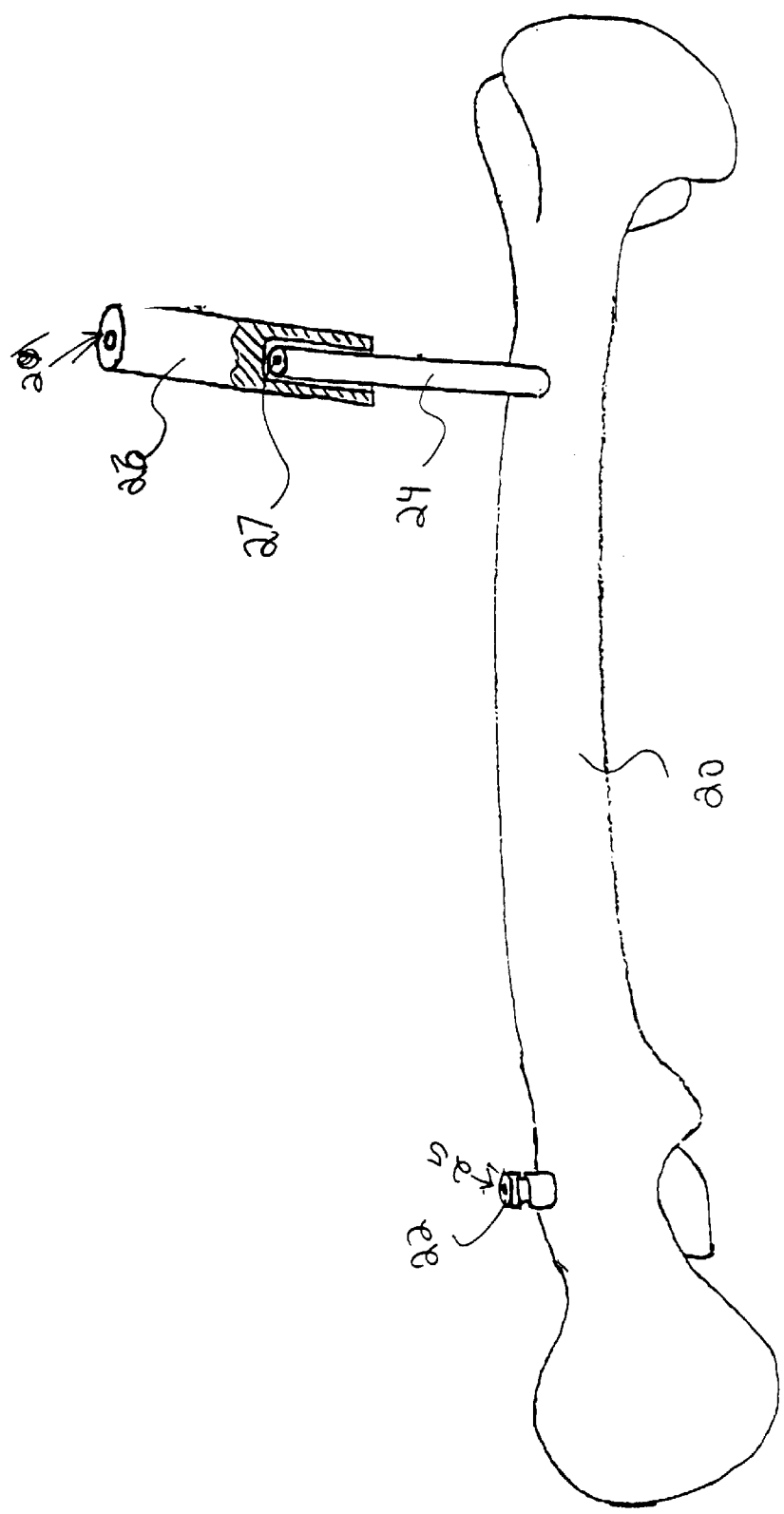

METHOD FOR DETERMINING THE LOCATION AND ORIENTATION OF A BONE FOR COMPUTER-ASSISTED ORTHOPEDIC PROCEDURES USING INTRAOPERATIVELY ATTACHED MARKERS

CROSS-REFERENCES TO RELATED APPLICATIONS

The present application is a regular application and claims the benefit of priority from U.S. Provisional Patent Application Ser. No. 60/112,321 filed Dec. 14, 1998, the complete disclosure of which is hereby incorporated herein by reference for all purposes.

TECHNICAL FIELD

The present invention relates to surgical bone cutting systems and more particularly to systems for detecting or tracking bone motion during surgery.

BACKGROUND OF THE INVENTION

When performing robotically assisted total hip replacement surgery, (for example, when cutting a cavity into a patient's femur bone for the insertion of an artificial hip joint therein), it is very important to minimize the effects of bone motion. Successful hip replacement surgery, particularly when using cementless implants, relies on the highly accurate creation of the cavity within the proximal (upper) end of the femur for receiving the implant. Deviations of less than plus or minus 1 mm from the planned cavity placement and dimensions are desirable.

Accordingly, to minimize the effects of unwanted bone motion on cutting accuracy, it has been desirable to attempt to prevent bone motion to the maximum degree possible by firmly anchoring the bone while the surgical bone cutter is operating on the bone. Typically, unwanted bone motion has been restrained by the use of fixators which hold the bone in position as firmly as is possible. Unfortunately, there are practical limits as to how securely the bone can be held in position by a fixator. For example, for many surgical procedures it is necessary for the surgical team to hand hold retractors for surgical access. Changes in the forces applied to the bone by these hand held retractors can cause unwanted bone motion. Moreover, in many cases the surgical team does not know whether additional retraction is required until after the bone cutting procedure has commenced. As such, it is typically necessary to modify or slightly change the retraction forces on the bone during the course of the bone surgery. This can have the undesirable effect of causing unwanted bone motion, leading to inaccuracies in cutting the bone. In addition, under some conditions, such as to provide optimal cutting access, it may even be desirable to move the bone slightly during surgery. This further complicates the problem of cutting inaccuracies caused by unwanted bone motion thereafter.

Small amounts of bone motion cause the surgical operative site to "drift", thereby causing undesirable implant cavity placement errors as the bone moves while a robotic bone cutter is cutting the implant cavity in the bone. Larger amounts of bone motion can cause serious cutting inaccuracies and are indicative of the bone fixation or retraction system becoming unstable. Should such larger amounts of bone motion occur, it is then necessary to immediately shut down the cutting operation and restart the cutting procedure after re-locating the position of the bone with respect to the cutting device. Specifically, the surgical team is required to remove the cutting device and its accompanying gas supply hose and irrigation, re-determine the position of the bone with respect to the cutting device, and then reinstall the cutter, gas supply, and irrigation systems before continuing with the bone cutting procedure. This can be very time consuming and frustrating for the surgical team.

SUMMARY OF THE INVENTION

As discussed above, unwanted bone motion can generate cutting inaccuracies during bone surgery. Such unwanted bone motion cannot be completely eliminated during bone surgery. Accordingly, the present invention provides a system to minimize the effects of unwanted bone motion by tracking the motion of the bone such that the unwanted bone motion can be compensated for during surgery on the bone.

The present invention provides a method for re-registration between a robotic coordinate system and an image data set, comprising: providing an image data set that has been registered within the robotic coordinate system based upon an initial bone position within the robotic coordinate system; locating at least three conserved points fixed relative to the initial bone position prior to a detectable change in bone position from the initial bone position; relocating the same at least three conserved points after bone motion may have occurred thereby determining changes in the position of the three conserve points; and re-registering the image data set within the robotic coordinate system based on the changes in position of the three conserved points.

In the present invention, intraoperatively attached fiducial markers are used to determine the position and orientation of the bone and to track bone motion over time. The intraoperatively attached fiducial markers are used to define at least three conserved points which are fixed relative to the bone. Bone motion is tracked over time by tracking the motion of the at least three conserved points over time.

In the present invention, the at least three conserved points (which are fixed relative to the bone), are located and tracked within the coordinate system of the surgical robotic arm subsequent to initially registering an image data set of the bone to the surgical robotic arm.

In one preferred aspect of the invention, the three conserved points are defined by two implanted fiducial markers. Preferably, at least one fiducial is implanted after the image data set of the bone, (which represents the shape of the bone), has been created.

First, the surgical robotic arm is registered to the bone. Initially registering the surgical robotic arm to the bone comprises determining the initial spatial relationship between the surgical robotic arm and the bone, (wherein the shape of the surface of the bone is preferably represented by an image data set).

The registration of the surgical robotic arm to the image data set of the bone can be accomplished using a variety of techniques. In certain aspects of the present invention, a variety of techniques using radio-opaque marker pins can be used.

For example, as is described in provisionally filed Patent Application entitled Bone Motion Tracking System, U.S. patent application Ser. No. 60/112,319 filed Dec. 14, 1998, and in non-provisionally filed U.S. patent application Ser. No. 09/247,818 filed on Feb. 9, 1999, incorporated herein by reference in their entirety for all purposes, marker pins are attached to the bone prior to surgery and a pre-surgical image of the bone with the marker pins attached is taken. The pre-surgical image can preferably be generated by computerized tomography (CT), digital radiography, or the like. From the image data set representing the pre-surgical image of the bone, the spatial relationship of the bone with respect to the marker pins can be determined, (ie: the position and orientation of the bone can be determined by knowing the position and orientation of the marker pins). In one aspect, the surgical robotic arm is registered to the bone by being moved to contact each of the marker pins in turn. As such, the position of each of the marker pins will be sequentially recorded in terms of the surgical robotic arm's co-ordinate system, thereby registering the surgical robotic arm to the bone. In other aspects, a digitizer arm, (which may comprise an articulated passive mechanical arm), is registered to the bone by being moved to contact each of the marker pins in turn. In this aspect, the digitizer arm is first registered to the robotic arm's coordinate system.

Alternatively, the present surgical robotic arm can be registered to the bone using marker pins by the system described in co-pending application Ser. No. 09/022,643, filed Feb. 12, 1998 now abandoned, and incorporated herein by reference in its entirety for all purposes, which describes a method and system for transforming a bone image into a robotic coordinate system based upon registering between the robotic coordinate system and the image data set: (1) two positional coordinates axially spaced apart along the bone and (2) a directional vector passing through at least one of the positional coordinates.

In alternate approaches, the present surgical robotic arm can be initially registered to the bone without the use of fiducial marker pins. For example, the initial position and orientation of the bone may be determined by an imaging system which relies upon sensing anatomical features of the bone. Such an imaging system may comprise an optical or ultrasound system which views the shape and location of the bone.

Alternatively, the surgical robotic arm can be registered to the bone without the use of fiducial marker pins by the system described in U.S. Pat. No. 5,806,518, incorporated herein by reference in its entirety for all purposes, in which a bone image is transformed into a robotic coordinate system by aligning a robotic probe within the medullary canal of the femur.

Alternatively, the surgical robotic arm can be registered to the bone without the use of fiducial marker pins by the system described in U.S. Pat. No. 6,033,415, incorporated herein by reference in its entirety for all purposes, which describes a method and system for transforming a bone image data set representing a bone image into a robotic coordinate system by registering a bone digitizer arm to the robotic coordinate system, generating a digitized bone data set by taking bone surface position measurements with the digitizer arm, and transforming the bone image data set into the robotic coordinate system by performing a best fit calculation between coordinates of the bone image data set and corresponding coordinates of the digitized bone data set.

Subsequent to registration of the surgical robotic arm to the bone, (using any of the techniques described above or any other technique), the locations of at least three conserved fiducial points fixed relative to the bone are then determined. Preferably, the three conserved points are fixed relative to the bone intraoperatively, and may be affixed to the bone subsequent to the initial registration of the surgical robotic arm to the bone.

The at least three conserved points are used to define a marker coordinate system to track the movement of the bone. Specifically, by tracking movement of the three conserved points, the corresponding movement of the bone can be determined.

An advantage of the present system of tracking bone movement by tracking movement of the three conserved points affixed to the bone is that a large degree of bone movement is possible without tracking being lost. In addition, it is possible to move the bone through a large degree of bone movement without mechanical tracking devices attached to the bone limiting the range of available bone movement.

The ability to achieve a large degree of bone movement during surgery may be advantageous for a number of reasons. For example, when performing computer assisted total knee replacement procedures, it is desirable to install a trail component and then take the knee through a set of motions. These motions generally require moving the limb over a large range of angles. These extensive movements make it very difficult to track both the femur and tibia when using bone tracking devices attached to the bone.

Another advantage of the present invention is that, by relying on a set of conserved points (located, tracked and preferably fixed relative to the bone after registration of the surgical robotic arm to the bone), the bone can be rapidly relocated without relying upon an anatomical features which may have been removed during the operative procedure.

By using three conserved marker points affixed relative to the bone during surgery, bone motion can be tracked regardless of changes to the features of the bone which may occur during surgery. This allows for refining cuts to be made in relation to previously cut surfaces, without relying on a preoperative fiducial marker system which may have been used to initially register the surgical robotic arm to the bone.

Additionally, by only tracking movement of the three conserved points subsequent to initial registration, (as opposed to tracking movements of a plurality of marker pins which may have been attached to the bone to initially register the surgical arm to the bone), any error components associated with the initial registration are not present in the tracking of the three conserved points.

Moreover, tracking movement of the present three conserved points can be performed much easier and faster than tracking bone movement by tracking a much larger number of surface location points on the bone, (wherein the surface location points define anatomical features of the bone).

The present invention is particularly advantageous for use with trauma cases or in reconstructive osteotomies where it is important to determine the position and orientation of multiple bone fragments and then track how they move. In such applications, features could be added to the fixture system defining the three conserved points such that it could be identified in fluoroscopy images after they are connected to the bone. In such applications, the fixture could be referenced in the images and then desired actions could be defined relative to the fixture coordinates.

In a preferred aspect, the present invention uses an articulated passive mechanical digitizing arm to identify the locations of the three conserved points, thereby generating a conserved point data set, (comprising coordinates representing the position of the conserved points which are affixed to the bone). The mechanical digitizing arm is preferably pre-registered to the robot coordinate system such that the positions of the three conserved points are determined in the robotic coordinate system. Alternatively, the locations of the conserved points may be determined by the surgical robotic arm itself.

The proximal end of the digitizer arm is preferably secured at a fixed location in the coordinate system of the surgical robotic arm. In particular, the proximal end of the digitizer arm is preferably secured to the frame of a robotic workstation from which the surgical robotic arm also extends. Being secured to the same fixture, relative motion between the coordinate systems of the surgical robotic arm and the digitizer arm is prevented.

An example of a suitable passive mechanical digitizer arm for use in conjunction with the present invention is found in U.S. Provisional Patent Application No. 60/112,319 filed Dec. 14, 1998 entitled Bone Motion Tracking System, subsequently filed as non-provisionally U.S. patent application Ser. No. 09/247,818 filed on Feb. 9, 1999, incorporated herein by reference in their entirety for all purposes. The system described in co-pending application entitled System and Method for Performing Image Directed Robotic Orthopedic Procedures without a Fiducial Reference System, now U.S. Pat. No. 6,033,415 on Sep. 14, 1998, is also incorporated herein by reference in its entirety for all purposes.

A conserved point data set is gathered by moving the distal end of the digitizer arm to contact each of the conserved points in sequence. The position of each of these conserved points is thereby determined and recorded forming the conserved point data set. Since the digitizer arm is reregistered to the robotic coordinate system, the conserved point data set will also be in the robotic coordinate system.

In a preferred aspect of the invention, the digitizer arm comprises an articulated linkage having high resolution position sensors at each joint. Using an embedded processor and appropriate software, the digitizer arm produces an accurate measurement of the position of its distal end relative to its proximal end. (It is to be understood, however, that the present digitizer arm may be substituted by a powered mechanical arm performing the same functions as described herein.)

In the present invention, the distal end of the digitizer arm is repeatably moved to contact each of the three conserved points such that movement of each of the three points can be tracked over time.

In the present invention, the three conserved points are located with only two marker structures attached intraoperatively to the bone. Specifically, the first marker structure comprises a fiducial marker pin and the second marker structure comprises an elongated shaft, (defining the second conserved point), with an extender received over the elongated shaft, (defining the third conserved point).

BRIEF DESCRIPTION OF THE DRAWINGS

FIG. 2A and 2B are top and elevation views of the distal bone marker.

FIG. 4 is a femur bone having a proximal bone marker and a distal bone marker and distal bone marker extender attached thereto.

DESCRIPTION OF THE SPECIFIC EMBODIMENTS

Referring first to FIG. 4, a femur bone 20 is shown with a proximal bone marker 22 and a distal bone marker 24 attached thereto. The attachment of proximal bone marker 22 and distal bone marker 24 to bone 20 is preferably made intraoperatively and subsequently to bone 20 being first registered to the coordinate system of a surgical robotic arm (not shown) using any of the varieties of techniques described above. It is to be understood, however, that proximal bone marker 22 and distal bone marker 24 can be attached to bone 20 prior to registration of bone 20 to the coordinate system of the surgical robotic arm.

Bone 20 is first registered to the coordinate system of the surgical robotic arm. Thereafter, the locations of points P1, P2 and P3, (which are defined by proximal bone marker 22 and distal bone marker 24, as will be explained), are first located and then tracked over time to track bone motion. Because the relationship between bone 20 and conserved points P1, P2, and P3 remains constant, motion of any or all of points P1, P2, and P3 corresponds identically to motion of bone 20.

Figure 1:
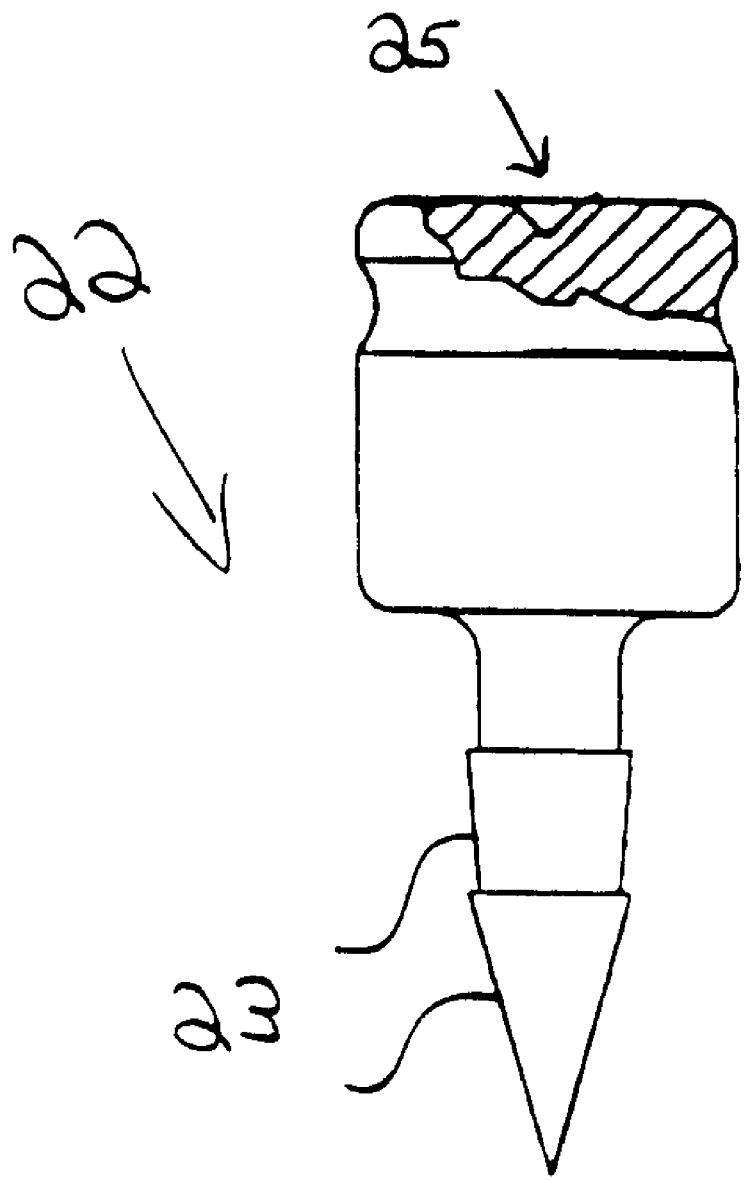
FIG. 1 is an elevation view of the proximal bone marker.

Details of proximal bone marker 22 are seen in FIG. 1. Bone marker 22 has at least one barb 23 for securing the bone marker into the bone. A conical locating feature 25 is found at the top end of proximal bone marker 22, defining conserved point P1, as shown. When the distal end of the digitizer arm (not shown) is brought into contact with conical locating feature 25, the exact position of conserved point P1 can be determined.

The digitizer arm preferably comprises a plurality of articulated links connected together at joints with a high resolution position sensor disposed in each joint. Using the high resolution position sensors and appropriate software, the digitizer arm can produce accurate measurements of the position of its distal end with respect to its proximal end. Preferably, rotation of the links about the joints permits the distal end to be moved in any of 6 degrees of freedom relative to its proximal end.

Details of distal bone marker 24 are seen in FIG. 2A and 2B. Distal bone marker 24 preferably comprises an elongated shaft having a conical locating feature 27 at its upper end, defining point P2, as shown. Distal bone marker 24 preferably comprises a drill tip 30 for drilling into bone 20 and threads 32 for holding and twisting distal bone marker 24 such that it firmly engages bone 20.

When the distal end of the digitizer arm (not shown) is brought into contact with conical locating feature 27, the exact position of conserved point P2 can be determined.

Figure 3B:
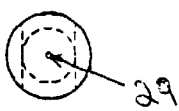
FIG. 3A and 3B are top and sectional elevation views of the distal bone marker extender.
Figure 3A:
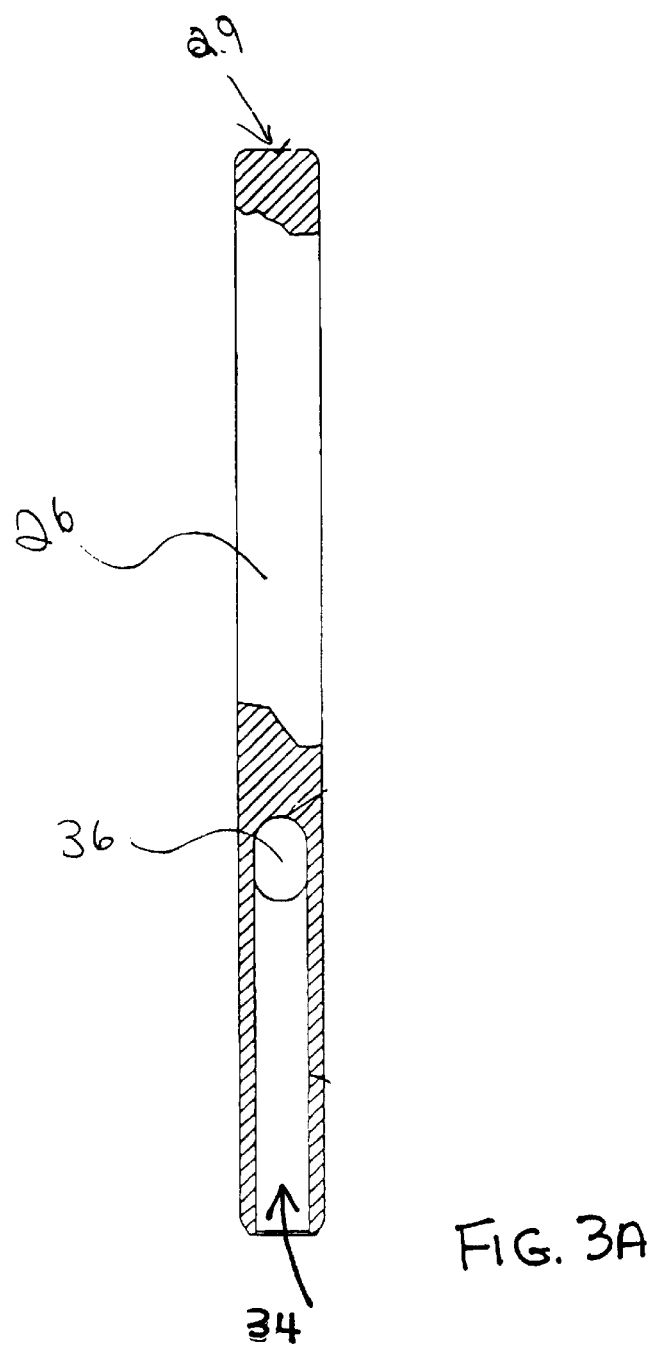

As seen in FIG. 4, a distal bone marker extender 26 is slipped over distal bone marker 24 as shown. Details of distal bone marker extender 26 are seen in FIG. 3A and 3B. Distal bone marker extender 26 also has a conical locating feature 29 disposed at its upper end, defining conserved point P3, as shown. Distal bone marker extender 26 is removable such that point P2 and point P3 can be repeatably and reliably measured with only one attachment made into bone 20.

Distal bone marker extender 26 has an opening 34 for receiving the top end of distal marker 24 therein, (as seen in FIG. 4). A hole 36 can be provided to view the contact between distal bone marker 24 and distal bone marker extender 26, thus ensuring the same spatial relationship exists between points P2 and P3 as distal bone marker extender 26 is removed and replaced. Specifically, the location of conserved point P2 is first determined (with distal bone marker extender 26 removed). Subsequently, distal bone marker extender 26 is received over distal bone marker 24 and the location of conserved point P3 is determined. Subsequently, distal bone marker extender 26 is removed and the location of conserved point P2 is re-determined, etc.

The positions of conical locating features 25, 27 and 29 which define conserved points P1, P2, and P3 are monitored over time, (preferably by repeatedly and sequentially contacting a distal end of a digitizer arm or the surgical robotic arm thereto). By measuring the movements of conserved points P1, P2, and P3 over time, (for example, by redetermining the positions of conical locating features 25, 27 and 29 with the distal end of a digitizer arm, or by any other method), the precise amount and direction of bone movement can be monitored over time. Accordingly, the motion of bone 20 can be tracked by repeatedly redigitizing points P1, P2, and P3.

An advantage of the present system of tracking bone movement by tracking movement of conserved points P1, P2 and P3 is that it is not necessary to redigitize bone surface points subsequent to registering the surgical robotic arm to the bone.

Conserved points P1, P2, and P3 are non-collinear and thereby define a three dimensional coordinate system. As points P1, P2, and P3 remain fixed relative to bone 20, motion of any or all of points P1, P2, and P3 will identically track motion of bone 20.

Figure 5:
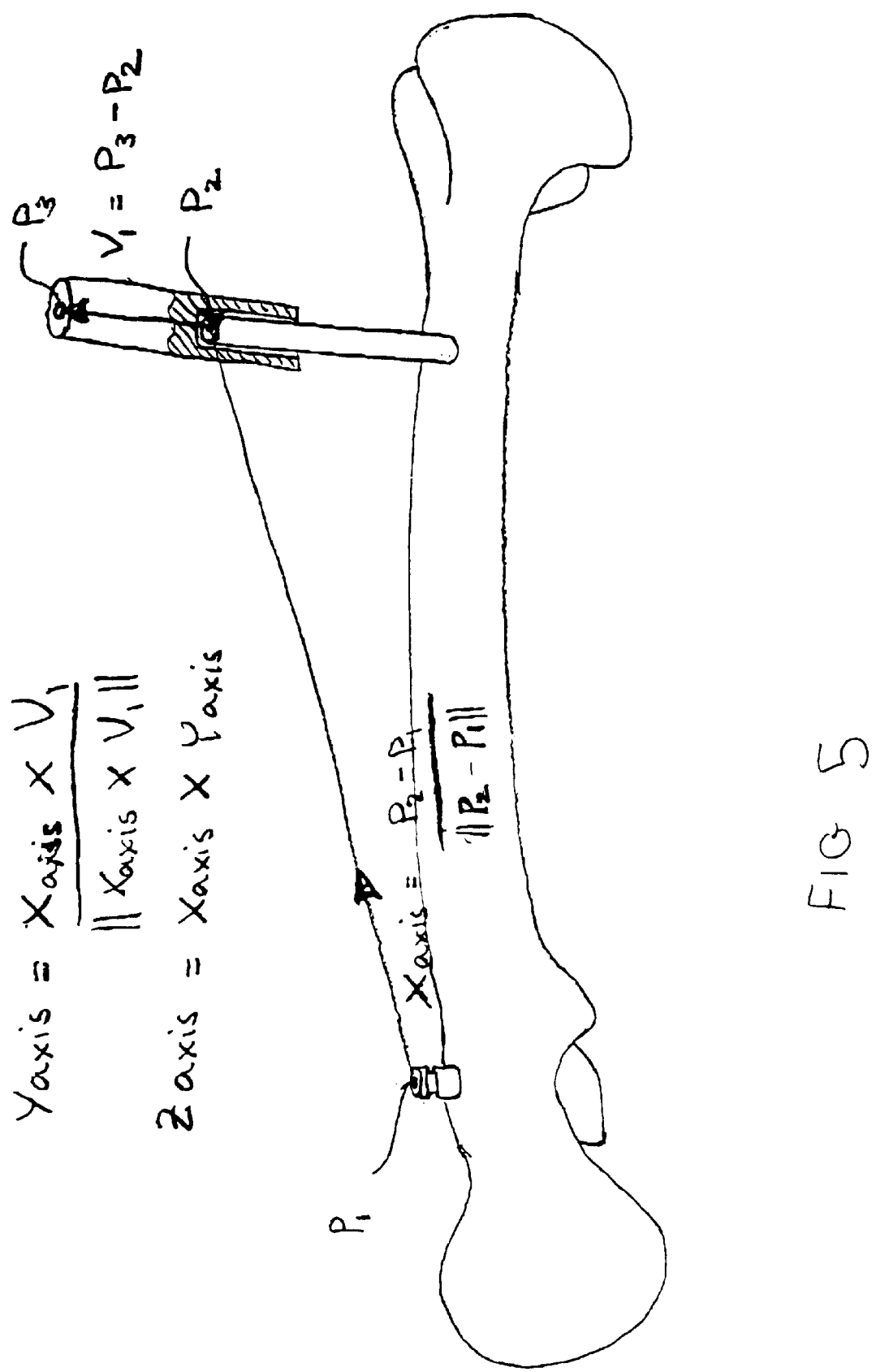
FIG. 5 is a vector diagram corresponding to FIG. 4.

In a preferred aspect of the present invention, the locations of conserved points P1, P2 and P3 are used to define a coordinate system as follows. Referring to the vector diagram of FIG. 5, the coordinate system is defined to have its origin at point P1. An x-axis is then defined between points P1 and P2 as follows:

$$X_{axis} = \frac{p_2 - p_1}{\|p_2 - p_1\|}$$

Another vector $v_2$ can be defined by $p_3$ and $p_2$, as $$v_2 = \frac{p_3 - p_2}{\|p_3 - p_2\|}$$

The Y axis is then defined as the unit vector of the cross product of the X axis and $v_2$ and the Z axis is defined as the cross product of the X and Y axes.

What is claimed is:

1. A method for re-registration between a robotic coordinate system and an image data set, said method comprising:

provide an image data set that has been registered within a robotic coordinate system based upon an initial bone position within the robotic coordinate system;

locate at least three conserved points fixed relative to the initial bone position prior to any detectable change in bone position from the initial bone position wherein a first conserved point is defined by a first fiducial marker and second and third conserved points are defined by a second fiducial marker;

relocate the first, second and third conserved points after bone motion may have occurred to determine the locational change in any of the first, second and third conserved points; and re-register the image data set within the robotic coordinate system based on the locational changes.

2. A method as in claim 1, wherein at least one of the first or second fiducial markers is implanted after the image data set has been created.

3. The method of claim 1, wherein at least one of the first or second fiducial markers is attached intraoperatively to the bone.

4. The method of claim 1, wherein locating the three conserved points is accomplished by contacting a distal end of a passive mechanical digitizing arm against each of the three conserved points.

5. The method of claim 1, wherein locating the three conserved points is accomplished by contacting a distal end of a surgical robotic arm against each of the three conserved points.

* * * * *